(12) United States Patent
Hood et al.

(10) Patent No.: US 10,940,053 B2
(45) Date of Patent: Mar. 9, 2021

(54) DISPOSABLE HYGIENE ARTICLE

(71) Applicant: Essity Hygiene and Health Aktiebolag, Gothenburg (SE)

(72) Inventors: Prelo M. Hood, Philadelphia, PA (US); Jozef Janek, Gemerska Horka (SK)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 0 days.

(21) Appl. No.: 16/479,759

(22) PCT Filed: Jan. 24, 2017

(86) PCT No.: PCT/SE2017/050062
§ 371 (c)(1),
(2) Date: Jul. 22, 2019

(87) PCT Pub. No.: WO2018/139962
PCT Pub. Date: Aug. 2, 2018

(65) Prior Publication Data
US 2019/0374396 A1    Dec. 12, 2019

(51) Int. Cl.
*A61F 13/15*     (2006.01)
*A61F 13/533*    (2006.01)
(Continued)

(52) U.S. Cl.
CPC .. *A61F 13/47218* (2013.01); *A61F 13/15634* (2013.01); *A61F 13/15747* (2013.01);
(Continued)

(58) Field of Classification Search
CPC ...... A61F 2013/51377; A61F 13/47218; A61F 13/15634
See application file for complete search history.

(56) References Cited

U.S. PATENT DOCUMENTS 4,556,146 A * 12/1985 Swanson ............... A61F 15/001
                                                        206/438
5,873,869 A *  2/1999 Hammons ......... A61F 13/15203
                                                        604/385.01
(Continued)

FOREIGN PATENT DOCUMENTS

CN      101065085 A      10/2007
CN      101636134 A       1/2010
(Continued)

OTHER PUBLICATIONS

Libraausnz, Ever put on a pad & think "hmmmm, have I even done that right?", Instagram post. Feb. 10, 2019 (Year: 2019).*
(Continued)

*Primary Examiner* — Michele M Kidwell
(74) *Attorney, Agent, or Firm* — Wood Herron & Evans LLP (57) ABSTRACT

The disclosure relates to a disposable hygiene article comprising an absorbent core which has first and second areas. The second area is located centrally in the middle portion of the article and extends longitudinally along a centre axis, transversally and symmetrically in a transverse direction towards each side edge of the core and in a thickness direction of the article. The second area protrudes outwards from a plane of the first area, and covers from 5-15% of a total area of the core. The first area surrounds the second area and covers the remainder of the total area of the core. The second area has grammage higher than grammage of the first area. The second area is integrated with the first area, and the second area is surrounded by a discontinuous embossing pattern which conforms to the shape of the second area of the core.

16 Claims, 3 Drawing Sheets

(51) Int. Cl.
   *A61F 13/513*   (2006.01)
   *A61F 13/472*   (2006.01)
   *A61F 13/514*   (2006.01)

(52) U.S. Cl.
   CPC ...... *A61F 13/51456* (2013.01); *A61F 13/533* (2013.01); *A61F 2013/15406* (2013.01); *A61F 2013/15715* (2013.01); *A61F 2013/51377* (2013.01)

(56) References Cited

U.S. PATENT DOCUMENTS

| | | | |
|---|---|---|---|
| 7,550,646 B2 | 6/2009 | Tamura et al. | |
| 8,173,858 B2 | 5/2012 | Kuroda et al. | |
| 8,558,054 B2 | 10/2013 | Noda et al. | |
| 8,715,258 B2 | 5/2014 | Munakata et al. | |
| 8,859,842 B2* | 10/2014 | Wilson | A61F 13/15756 604/379 |
| 9,248,060 B2 | 2/2016 | Noda et al. | |
| 2003/0078553 A1* | 4/2003 | Wada | A61F 13/42 604/361 |
| 2006/0116652 A1 | 6/2006 | Miura et al. | |
| 2006/0276767 A1 | 12/2006 | Ueminami et al. | |
| 2010/0069868 A1 | 3/2010 | Noda et al. | |
| 2011/0130737 A1* | 6/2011 | Sagisaka | A61F 13/4704 604/380 |
| 2011/0251575 A1 | 10/2011 | Kuroda et al. | |
| 2013/0267926 A1* | 10/2013 | Uematsu | A61F 13/4758 604/385.101 |

FOREIGN PATENT DOCUMENTS

| | | |
|---|---|---|
| CN | 101646408 A | 2/2010 |
| CN | 102026604 A | 4/2011 |
| CN | 102264326 A | 11/2011 |
| CN | 104684517 A | 6/2015 |
| EP | 1917939 A1 | 5/2008 |
| EP | 2133052 A1 | 12/2009 |
| EP | 2324806 A1 | 5/2011 |
| EP | 2380542 A1 | 10/2011 |
| EP | 2601920 A1 | 6/2013 |
| JP | 2010125199 A | 6/2010 |
| JP | 2011120696 A | 6/2011 |
| JP | 2011255116 A | 12/2011 |
| JP | 2013255552 A | 12/2013 |
| RU | 2454981 C2 | 7/2012 |
| RU | 2520901 C2 | 6/2014 |
| RU | 2581114 C1 | 4/2016 |
| WO | 9515139 A1 | 6/1995 |
| WO | 0197736 A1 | 12/2001 |
| WO | 2012029848 A1 | 3/2012 |

OTHER PUBLICATIONS

International Preliminary Report on Patentability for International Application No. PCT/SE2017/050062, dated Apr. 10, 2019—16 pages.

International Search Report and Written Opinion for International Application No. PCT/SE2017/050062, dated Oct. 3, 2017—16 pages.

Chinese Office Action for Chinese Application No. 201780084201.6, dated Nov. 6, 2019, with translation, 11 pages.

Federal Service for Intellectual Property, Decision to Grant, Russian Application No. 2019126439, dated Apr. 17, 2020, with translation, 18 pages.

European Patent Office, Extended European Search Report issued in corresponding EP Application No. 17894223.1, dated Jun. 24, 2020 (7 pages).

The State Intellectual Property Office of People's Republic of China, Third Office Action, Application No. 201780084201.6, dated Jul. 2, 2020 (20 pages).

Chinese Office Action for Chinese Application No. 201780084201.6, dated Feb. 26, 2020, with translation, 18 pages.

China National Intellectual Property Administration, Decision of Rejection, Chinese Application No. 201780084201.6, dated Nov. 26, 2020, 14 pages.

\* cited by examiner

Fig. 4a    Fig. 4b

DISPOSABLE HYGIENE ARTICLE

CROSS REFERENCE TO RELATED APPLICATIONS

This is a U.S. National Phase application of PCT/SE2017/050062, filed Jan. 24, 2017, the disclosure of which is incorporated herein by reference in its entirety for all purposes.

TECHNICAL FIELD

The present invention relates to a disposable hygiene article and to a method of manufacturing the disposable hygiene article.

BACKGROUND

For disposable hygiene articles, such as sanitary napkins, there are high requirements that they are discreet, soft and comfortable to wear and at the same time have a reliable security against leakage. Such disposable hygiene articles or products usually comprise a liquid permeable topsheet, a liquid-impermeable backsheet, and an absorbent core enclosed there between.

For sanitary napkins intended to absorb bodily liquids such as urine and menstrual liquid, which is more viscous than urine, it is important that there is sufficient absorbency of the liquids in a liquid receiving portion of the sanitary napkin which is often in the central area of the napkin. Further, menstrual liquid may easily move around on the user facing side of a topsheet under the influence of gravity, motion and pressure by the user. Migration of menstrual liquid to the edges of the article increases the likelihood of leakage, and further smears the menstrual liquid against the skin of the user making cleanup more difficult. It is desirable that articles used for absorbing menstrual liquids are able to give the user a feeling of secureness and a visual impression that the menstrual liquid is absorbed by the absorbent core. Further, it is desired to minimize the cost of manufacturing the absorbent articles.

There have been several attempts in the prior art to improve comfort of the absorbent articles. For example EP2324806 discloses an absorbent article in which grooves are provided to prevent leakage by preventing generation of a gap between a user's body and the absorber. EP2380542 from the same applicant also deals with keeping a body liquid contacted with a compressed groove from diffusing to an end part of the compressed groove and prevent the absorbent article from deforming due to contact with a body liquid. JP2013-255552 discloses another absorbent article in which fit is improved and leakage prevented by providing a front and a rear two-layer absorbent body and embossing lines. However, the structure of the article is complex.

However, even though there have been attempts to improve the leakage control and comfort of the articles, there is still a need for further improved comfort and leakage control in disposable hygiene articles. Also, there is a need for a simplified manufacturing process for such disposable hygiene articles.

SUMMARY

The objective of the present disclosure is to improve the comfort and leakage control of a disposable hygiene article. It is an object to provide an article that adapts to the anatomy of the user while liquid absorbing properties are improved.

Also, it is an aim to provide a disposable hygiene article which is easy to attach in a correct position to underwear of the user.

Furthermore, it is an object to provide a disposable hygiene article which can be folded without deteriorating the properties of an absorbent core in the liquid receiving portion of the article.

Further, it is an objective to provide a disposable hygiene article and a package thereof which are easy to manufacture.

The objectives above are attained by a disposable hygiene article, a package including the article and a method for manufacturing the article as defined by the appended claims.

Especially, the objectives above are attained by a disposable hygiene article comprising a liquid-permeable topsheet, a liquid-impermeable backsheet and an absorbent core comprising an absorbent material, the core being arranged between the topsheet and backsheet. The article has a longitudinal centre axis dividing the article into a first longitudinal portion and a second longitudinal portion, which have a symmetrical and mirror imaged shape in relation to each other. The article comprises a front portion, a middle portion and a rear portion in the longitudinal direction of the article, each portion having an individual shape. The article is adapted for three-fold. The three-fold can be performed along transverse folding axes which correspond to non-visible lines dividing the article into the front, middle and rear portions. According to the present disclosure, the absorbent core comprises a first area and a second area. The second area is located centrally in the middle portion and extends longitudinally along the centre axis. Further, the second area extends transversally and symmetrically in a transverse direction towards each side edge of the core and in a thickness direction of the article such that it protrudes outwards from a plane of the first area. The second area covers from 5-15% of a total area of the core. The first area surrounds the second area and covers the remainder of the total area of the core. Further, the second area has a grammage higher than the grammage of the first area and the second area is integrated with the first area. Further, the second area is surrounded by a discontinuous embossing pattern which conforms to the shape of the second area of the core.

By providing the core with a centrally located second area which has a higher grammage than the surrounding first area, which second area is integrated with the first area and additionally surrounded by a discontinuous embossing pattern an article or a product with high comfort which adapts to the anatomy of the user is provided. The second area provides for improved absorbent capacity in the middle portion of the article, where most of the liquid to be absorbed is received. Since the second area of the core is integrated with the first area, there is no need for separate sheets or layers and the manufacture of the article is facilitated and made for flexible. Therefore, the leakage control of the article is improved. The embossing pattern affects the liquid distribution in the core so that the embossing pattern provides borders through which the liquid can travel, but whereby the travel is at least partly obstructed. However, since the pattern surrounding the second area is discontinuous, the liquid can flow to other portions of the core and thus the liquid can be distributed along the core easily at least through openings in the pattern if necessary. Thus, the leakage control is further improved. Furthermore, the embossing pattern improves visual effects and thus, the embossing pattern surrounding the second area aids in attaching the article in a correct position to underwear of the user.

The grammage of the absorbent material in the first area can be from 400-600 g/m². The grammage of the absorbent material in the second area can be from 600-900 g/m². In this way maximal absorbency can be provided while the article is still comfortable to wear.

The discontinuous embossing pattern may comprise two longitudinally extending embossing lines, one on each side of the second area, and two distinct transversal lines in proximity of each longitudinal end of the second area. The transversal embossing lines are shorter than the transversal distance between the longitudinally extending embossing lines. In this way, the pattern can visually aid in positioning of the article in correct position. The two longitudinally extending embossing lines may extend along each of the front portion, middle portion and rear portion of the article. In this way liquid distribution along the whole length of the core can be controlled.

The folding axes for the three-fold can be located longitudinally outside the transversal embossing lines towards the longitudinal ends of the article. In this way, the disposable hygiene article can be folded without deteriorating the properties of the second area of the absorbent core in the liquid receiving middle portion of the article.

The second area of the core has substantially an oval shape and has a longer extension in the longitudinal direction than in the transverse direction. In this way the article and especially the second area of the core adapts better to the anatomy of the user.

The embossing pattern preferably corresponds to a substantially convex pattern in the middle portion and transitions to concave pattern in the transition region between the front portion and the middle portion. In this way the embossing pattern corresponds to the oval shape of the second area.

The embossing pattern can correspond to a substantially open ended heart-shaped pattern in the front portion. The longitudinally extending embossing lines preferably taper to form a concave pattern in the transition region between the front portion and the middle. In this way an aesthetically pleasant shape is provided, while the liquid retaining properties are improved and thus the leakage control is further improved, since the heart shaped end portion towards the front edge of the core in the front portion of the article prevents at least partly the liquid from flowing over the front edge of the core.

The embossing pattern forms two substantially U-shaped portions in the rear portion. The U-shaped portions adapt the article better to the anatomy of the user or wearer and thus the comfortability of the article is further improved.

The hygiene article may comprise additional embossing patterns in at least one of the front portion, the transitional area between the front portion and the middle portion, and/or the middle portion. The additional embossing patterns may further control the liquid distribution in the article.

The article may further comprise a liquid acquisition sheet located next to the topsheet and towards the core. Also a further protective sheet can be arranged between the liquid-impermeable backsheet and the absorbent core. By providing a liquid acquisition sheet, the liquid distribution may be improved. By providing a further protective sheet, mainly the embossing equipment, but also the core can be protected during the manufacture of the article.

The absorbent material in the core is preferably free of super absorbent polymers (SAP). Thus, a thicker article than an article comprising SAP is provided, whereby a feeling of more security against leakage is provided while the comfort of the article can be improved.

The second area of the core is preferably thicker than the first area of the core and the thickness of the first area of the core can be from 3 to 7 mm and the thickness of the second area of the core can be from 7 to 10 mm. Thus, the absorbent capacity is maximized while the article is still comfortable to wear. Since the core and thus the article is thicker in the second area of the core, it provides for secure feeling against leakage while the thinner first area provides for more comfort in use.

The embossing lines can be obtained by means of high compression embossing, which is suitable to obtain sufficiently visible embossing pattern in the article.

The embossing lines can be formed by means of an embossing pattern comprising individual circles placed in a predetermined pattern having an equal diagonal and lateral mutual distance from each other. In this way, the visibility of the pattern is secured while the materials are protected during the manufacture.

The second area of the core is suitably free of high compression embossing. Thereby, the second area will be thicker in the thickness direction than the first area of the core and thus it will conform to the anatomy of the user.

The present disclosure also relates to a method for the manufacture of the disposable article defined above. The method comprises the steps of:

feeding a liquid-permeable top sheet material layer, a liquid-impermeable backsheet material layer and an absorbent material arranged to be located in between the topsheet material layer and the backsheet material layer, forming the absorbent core so that it comprises a first area and a second area by feeding in a continuous flow absorbent material to form the core, whereby a larger amount of the absorbent material is formed in the second area of the core than is formed in the first area of the core, wherein the core absorbent material is formed such that the first area surrounds the second area located centrally in the middle portion and extending longitudinally along the centre axis, symmetrically in a transverse direction towards each side edge of the core and in a thickness direction of the article such that it protrudes outwards from the plane of the first area, the second area covering from 5-15% of a total area of the core, the first area surrounding the second area and covering the remainder of the total area of the core, the second area having a density higher than the first area and wherein the second area is integrated with the first area, and embossing a discontinuous embossing pattern to the topsheet layer and the absorbent core, or to the layers comprising the topsheet layer and the absorbent core, the pattern conforming to the shape of the second area of the core, the pattern comprising two longitudinal and two transversal embossing lines that surround the second area, such that the second area is free of compression during the embossing.

The core forming step may comprise compression of the core. The core compression may occur in three stages. All areas, i.e. both the first and second areas of the core are compressed during a first stage. The first area is further compressed during a second stage in which the second area is protected from too much compression. The first area is compressed even more during the high compression embossing. However, the second area is still protected from further compression during the embossing stage, which is suitably high compression embossing stage.

The method may further comprise folding the article by means of three-fold along folding axes that are arranged longitudinally outside the transversal embossing lines towards the longitudinal ends of the article. In this way the second area of the core will not be affected by the folding and thus the absorbent properties will not be negatively affected.

The method may further comprise providing a liquid acquisition sheet next to the topsheet and towards the core, and providing a protective sheet between the liquid-impermeable backsheet and the absorbent core to protect the core and embossing equipment during embossing. The protective sheet can be thus located beneath the absorbent core directly adjacent to and in contact with the absorbent core.

The present disclosure further relates to a package containing the disposable hygiene article as defined above. The disposable hygiene article may be folded in the package.

Further features and advantages are described more in detail below with reference to the appended drawings.

DETAILED DESCRIPTION OF PARTICULAR EMBODIMENTS

Disposable hygiene articles are absorbent articles aimed for personal hygiene and are arranged to absorb body exudate, such as blood or urine. Such disposable hygiene articles are single-use articles, for example adult incontinence articles, sanitary towels and panty liners.

The disposable hygiene article of the present disclosure comprises a liquid-permeable topsheet, a liquid-impermeable backsheet and an absorbent core comprising an absorbent material. The core is arranged between the topsheet and backsheet. By liquid-permeable is meant that liquid, such as urine or blood or water, can pass through the material. By liquid-impermeable is meant that liquid, such as urine or blood or water, cannot pass through the material. By absorbent material is meant material that is capable of absorbing or soaking up liquid.

Figure 1:
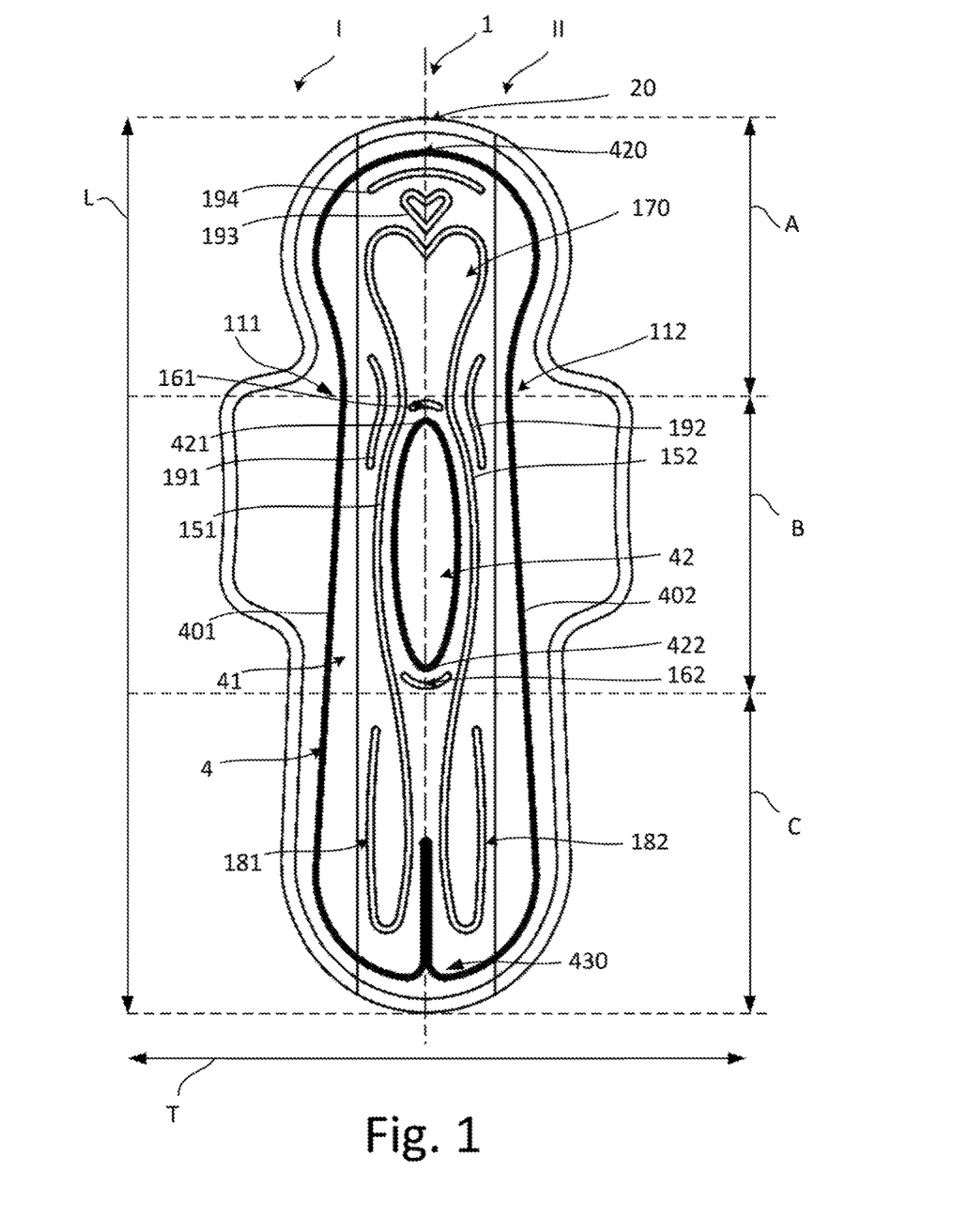
FIG. 1 shows an example of a disposable hygiene article according to the present disclosure from above.

The article has a longitudinal centre axis L dividing the article into a first and a second longitudinal portion each of which has a symmetrical and mirror imaged shape in relation to each other. In FIG. 1 it is shown that the article 1 comprises a front portion A, a middle portion B and a rear portion C in the longitudinal direction of the article and each portion has an individual shape. The article is adapted for three-fold when the article is individually packaged for delivery to a consumer.

Generally, the disposable hygiene articles are releasably attachable on a garment, suitably an undergarment of a user by means of an adhesive material.

The topsheet has a body facing surface which is aimed to be in contact with skin of the user for example in a crotch area of the article and thus face the user. The topsheet also has a garment facing surface which is on the opposite side of the topsheet and thus faces towards the garment of the user and therefore away from the user when the article is worn by the user. The liquid-impermeable backsheet also has a body facing surface and a garment facing surface.

The disposable hygiene article suitably has an essentially hourglass-shaped outer contour in the plane defined by the longitudinal and transverse extension of the disposable hygiene article, but other shapes, such as asymmetrical shapes are also conceivable. The disposable hygiene article may comprise at least one flap or "wing" that extends in transverse direction of the article outside the longitudinal sides of the core. The wings may be prolonged portions of the backsheet and/or topsheet in the transverse direction of the disposable hygiene article to create the at least one flap extending along any of the longitudinal sides of the core. The wings may also be provided by separate pieces of material which are attached to the backsheet and/or topsheet material for example by gluing. Usually there are two flaps, one on each longitudinal side of the absorbent core. The at least one flap is suitably provided with pressure sensitive adhesive affixed to the garment facing surface of the backsheet.

Normally, the absorbent core is smaller than the backsheet and/or topsheet in a plane of the longitudinal and transverse extension of the backsheet and/or topsheet. In this case the body facing surface of the backsheet is joined to the garment facing surface of the topsheet and the core is located inside the area where the backsheet is joined to the topsheet.

Alternatively, the core and at least the topsheet have substantially the same extension in a plane of the longitudinal and transverse extension of the absorbent article. The topsheet can be joined together with the subjacent backsheet and the absorbent core, for example by means of adhesive, ultrasonic joining or by means of some form of thermal bonding.

The topsheet and backsheet may extend in transverse direction of the article outside the longitudinal sides of the core. As explained above, at least the backsheet may be further prolonged in the transverse direction of the article to create at least one flap extending along any of the longitudinal sides of the core. Alternatively, also the topsheet is further prolonged in the transverse direction of the article to create at least one flap extending along any of the longitudinal sides of the core, the topsheet and the backsheet forming a laminate in the flap. The flaps can then be used to be folded around the leg openings of the briefs, and thus provide an improved leakage protection and secure attachment to the garment of the user.

The absorbent article may comprise further layers or sheets, such as an admission layer or sheet, also called an acquisition sheet, which is located beneath the topsheet, and also suitably in contact with the garment facing side of the topsheet. The acquisition sheet is intended to quickly absorb liquid and spread the liquid before it is transported to the absorbent core, where it is retained. The acquisition sheet preferably comprises low grammage air-laid or wadding. The acquisition sheet can be joined with the topsheet. The topsheet and the optional acquisition sheet may be attached together by embossing or by means of ultrasonic processing to form a laminate. If the layers are attached together by means of ultrasonic processing, at least one of the topsheet or acquisition sheet comprises a thermoplastic material. The other layers or sheets of the article may be laminated together or the other layers may be attached together by means of embossing or adhesive. When laminated together the sheets are joined by means of a reinforcement executed with ultrasonic processing essentially along the peripheral edge of the sheets that forms an edge seal of the laminate so that the risk of any leakage and spread of liquid via the peripheral edge is minimized or eliminated. The reinforcement can extend from the periphery and towards the inside of the article for a distance of about 2-6 mm.

The topsheet usually includes regenerated cellulose fibers, polyester or other synthetic polymer fibers, or films and is provided on the body-facing side of the disposable hygiene article, i.e. on the side that is aimed to face the body of the user when the article is worn. The topsheet is provided for comfort and conformability and directing the liquid to the underlying absorbent core. The liquid-permeable topsheet is preferably manufactured from a material that exhibits characteristics such as dryness and softness during the time when the absorbent article is being worn, because the topsheet is in contact with the user's body. It is also desirable for the topsheet to have a soft and textile-like surface which remains dry, even in the event of repeated wetting. The topsheet can consist of a nonwoven material, for example, with a soft and smooth surface, such as a spunbond material made from polypropylene fibres. A perforated, hydrophobic nonwoven material may be used in order to permit the surface that is closest to the user's body to be kept dry, in conjunction with which openings are formed in the material that are larger than the holes between the fibres in the material. In this way, liquid can be led down through the perforated openings in the topsheet to the subjacent absorbent core. Other examples of materials for the topsheet are perforated plastic films such as a perforated polyester film attached to a nonwoven sheet (usually called laminate). The nonwoven part of the topsheet can also be a spunbond nonwoven material, an air-through nonwoven material, a spunlace nonwoven (hydroentangled) material, a meltblown nonwoven material, or a combination of these, such as a SMS-material, which is a layered product including spunbond-meltblown-spunbond nonwoven materials. The raw material can be polypropylene (PP), polyethylene (PE) polyester (PET), polyamide (PA), or a combination of these. If a combination is used, this can be a mixture of fibres from different polymers, although each fibre can also include different polymers (e.g. PP/PE bi-component fibres or PP/PE copolymers). Where appropriate, the plastic film can consist, as non-limiting examples, of PE or PP, PET, PLA or amyl (or, for that matter, any other thermoplastic polymer), or a mixture or copolymers of the aforementioned polymers. The topsheet preferably comprises a spunbond material comprising polypropylene fibres which provide for optimal comfort and handleability of the product. Other suitable fibres for making the nonwoven material are for example natural fibres such as bamboo, cotton and flax.

The absorbent core is appropriately manufactured from a suitable fibre material in the form of natural or synthetic fibres with absorbent characteristics, or a mixture of natural fibres and synthetic fibres or other absorbent materials of a previously disclosed kind that are suitable for use in, for example, sanitary towels, incontinence pads and panty liners. The absorbent core may comprise one or more layers of defibrillated cellulosic fibres, for example cellulose fluff pulp. Other materials, which may be used, are for example absorbing or wettable nonwoven materials, foam materials, synthetic fibre materials or peat.

The absorbent core according to the present disclosure is preferably free of superabsorbent material. Thus, the core of the present article is arranged thicker than in the articles comprising superabsorbent material normally in an amount of 10 to 30% by weight, whereby the comfort and the fit of the article may be improved. Alternatively, the core may comprise only a minor proportion, i.e. less than 10%, for example 1-5% by weight of the core, of superabsorbent material.

The super absorbent material may be polymeric materials in the form of particles, fibres, flakes or the like, and the material possesses the ability to absorb and chemically bind liquid equivalent to several times their own weight to form an aqueous gel. This imparts a very high liquid-absorbent capacity to the finished absorbent article or product while the product is still soft and easy to handle and manufacture.

The absorbent core of the present disclosure is generally smaller than the article as a whole, defined by the outer contours of the article. The core may have a shape corresponding to the outer contours of the article defined suitably by the topsheet or other sheets in which the optional wings or flaps are excluded. Alternatively, the shape of the core may be different from the outer contours of the article.

The core is of a unitary construction. By "unitary construction" in the present context is meant that the absorbent core is constructed from essentially one type of material, this being essentially the same material, or essentially the same combination of two or more materials throughout the absorbent core. Variations in grammage and concentration of the material occur by means of the core having a first region and a second region, but these are limited to those which may be obtained without incorporation of regions which have been formed separately and then physically joined to each other. For example, when the absorbent core comprises a matrix of an absorbent material with absorbent characteristics, e.g. hydrophilic fibres, and optionally a superabsorbent material, the relative concentrations of superabsorbent material and fibres may be different in different parts of the core. The absorbent material could also be a hydrophobic material that has the capability to retain liquid within the structure of the material. However, when the construction is unitary, the absorbent core does not, for instance, comprise layers or laminates of different composition. Likewise, variations in the density, surface weight or concentration of various components across the longitudinal direction, the transverse direction or the thickness direction of the absorbent core may occur.

The absorbent core of the present disclosure comprises a first area and a second area. The second area is smaller than the first area and is arranged centrally in the core. The first area surrounds the second area and covers the remainder of the total area of the core. The second area of the core has a grammage which is higher than the grammage of the first area. The second area is integrated with the first area. By integrated is meant that the core comprising the first and the second areas has a unitary construction and that the areas are obtained in a manufacturing process by increasing the amount of the absorbent core material in the second region. The increased amount and thus the higher grammage of the "second area" is obtained by having forming molds in the manufacturing process that are configured to hold more material in the second area than is held in the first area. Thus, the design of the molds enables the distribution of absorbent material in the present core into two different areas. Therefore, a higher grammage in the second area is obtained. Thus, since the second area is integrated with the first area, the second area is obtained without incorporation of regions which have been formed separately and then physically joined to each other.

Further, according to the present disclosure, the second area of the core is surrounded by a discontinuous embossing pattern which conforms to the shape of the second area of the core. By embossing pattern is meant a pattern which is sunken into the surface of the topsheet material and the core and any layer in between the topsheet and the core. The embossing pattern may be produced by embossing. The embossing pattern can be obtained by using high compression embossing/debossing in which a die corresponding to the desired embossing pattern is used. Embossing occurs before the marriage of the backsheet layer to other layers of the absorbent article. The topsheet, the protective layer, and all layers disposed there between are embossed.

However, the backsheet is not subjected to embossing. The die comprises an area corresponding to the second area of the core in which no pressure is applied to the material to be embossed. In this way, the second area will retain a higher thickness than the surrounding first area of the core, while also the grammage of the second area of the core is higher than in the first area of the core. In this way an improved absorption capacity is obtained in the second area.

Reference is now made to FIGS. 1, 2, 3, 4a and 4b in which an example of a disposable hygiene article and parts thereof are shown. The disposable hygiene article 1 comprises a liquid-permeable topsheet 10, a liquid-impermeable backsheet 13 and an absorbent core 4 comprising an absorbent material, see FIGS. 1 and 2. The core 4 is arranged between the topsheet 10 and backsheet 13. The article has a longitudinal centre axis L dividing the article into a first and second longitudinal portion (I; II) which have a symmetrical and mirror imaged shape in relation to each other. The article comprises a front portion A, a middle portion B and a rear portion C in the longitudinal direction L of the article 1. Each portion has an individual shape. The article is adapted for three-fold and can be folded along two folding axes, wherein the first folding axis is a transversal line dividing the article into the front portion A and middle portion B, and the second folding axis is a transversal line dividing the article into the middle portion B and rear portion C. Alternatively, the first folding axis can be the transversal line dividing the article into the middle portion B and rear portion C, and the second folding axis can be the transversal line dividing the article into the front portion A and middle portion B. The article may be individually packaged by for example wrapping a thin plastic material around the article.

Figures 4A, 4B:
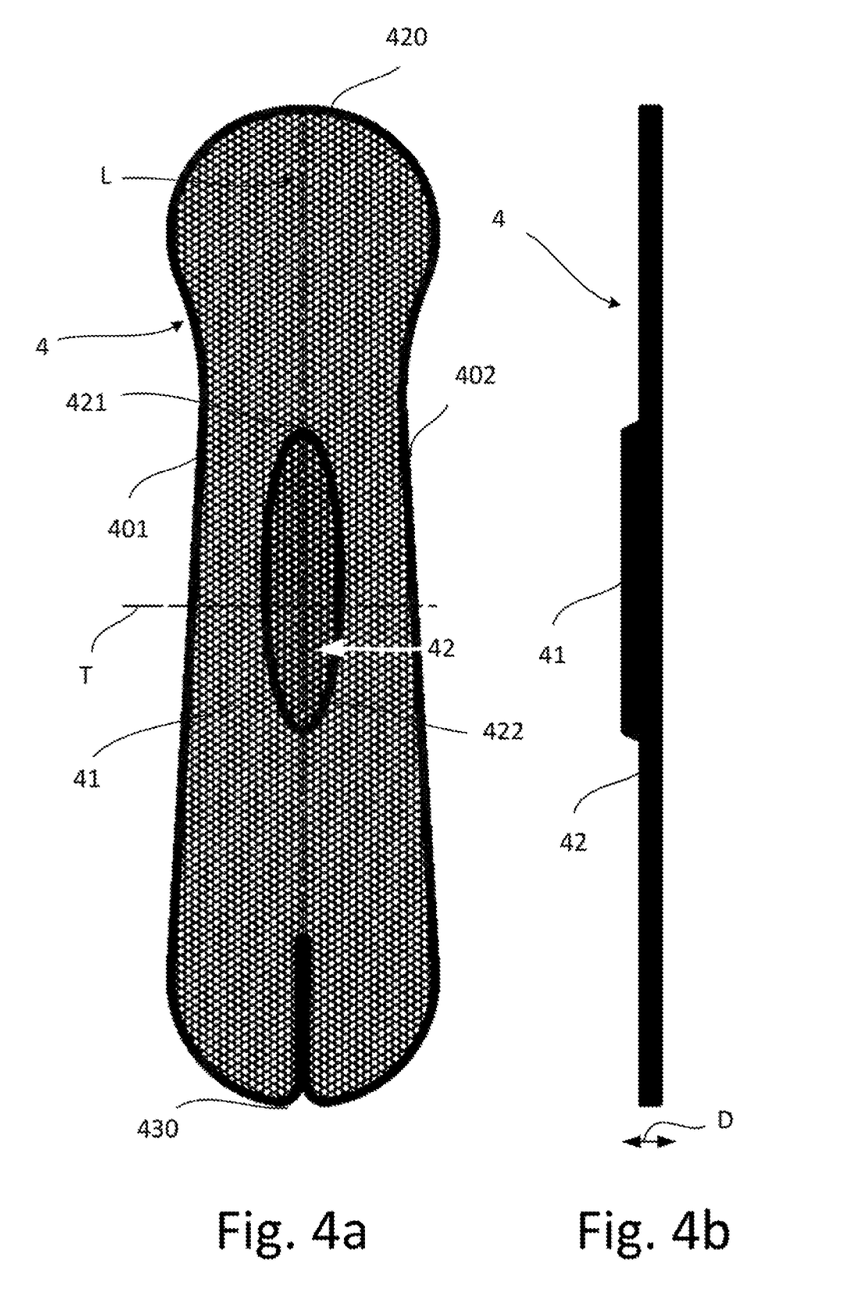
FIG. 4a shows an absorbent core from above
FIG. 4b shows the absorbent core of FIG. 4a in a side view.

The absorbent core 4, which is best shown in FIGS. 4a and 4b, comprises a first area 41 and a second area 42. The second area is located centrally in the middle portion B and extends longitudinally along the centre axis L, transversally and symmetrically in a transverse direction T towards each side edge 401; 402 of the core. Further the second area extends in a thickness direction D of the article such that it protrudes outwards from the plane of the first area in the thickness direction D, as best shown in FIG. 4b.

The second area 42 suitably covers from 5-15% of a total area of the core 4. The first area 41 surrounds the second area and covers the remainder of the total area of the core 4. The second area has a surface weight or grammage (weight of the absorbent material in grams/area of the absorbent material in square meters) higher than the surface weight or grammage of the first area. Further, as explained above, the second area is integrated with the first area.

Further, in an embodiment, it is essential that the second area is surrounded by a discontinuous embossing pattern which conforms to the shape of the second area of the core. By discontinuous is meant that the embossing pattern surrounding the second area is not continuous, i.e. there are openings in the pattern. By having openings in the pattern surrounding the second area, the flow of liquid outside of the second area is facilitated, and the absorbent properties and the comfort of the article can be improved.

A variant of a discontinuous embossing pattern is shown in FIG. 1 and comprises two longitudinally extending embossing lines 151; 152, one on each side of the second area 42, and two distinct transversal lines 161; 162 in proximity of each longitudinal end 421; 422 of the second area 42. The transversal embossing lines 161; 162 are shorter than the transversal distance between the longitudinally extending embossing lines 151; 152, whereby a discontinuous embossing pattern surrounding the second area is obtained. The longitudinally extending embossing lines 151; 152 have a length that is sufficient to extend into each of the front portion A, middle portion B an rear portion C in the longitudinal direction L of the article 1, and along the whole length of the middle portion B.

As shown in FIG. 1, the second area 42 has an oval shape. By oval shape is meant in this connection an essentially oval shape, whereby small variations in the shape may be possible. The second area 42 has a longer extension in the longitudinal direction (L) than in the transverse direction (T). Both the longitudinally extending embossing lines 151; 152 and the transversal embossing lines 161; 162 are suitably curved to adapt to the shape of the second area. In this way liquid can be equally distributed along the sides of the first area that surround the second area.

The embossing pattern suitably corresponds to a substantially convex pattern in the middle portion B and transitions to concave pattern in a transition region 111; 112 between the front portion A and the middle portion B. Further, the embossing pattern corresponds to a substantially open ended heart-shaped pattern 170 in the front portion A and the longitudinal embossing lines 151; 152 taper to form a concave pattern in the transition region 111; 112 between the front portion A and the middle B portion. Thus by open ended is meant that the lines forming a mirror-imaged convex pattern, or a pattern in which two arc-shaped lines protrude outwards towards the edges of the core from a common central starting point, in an upper end of the heart shaped-pattern do not meet in a lower end, i.e. at the end towards the middle portion B, of the heart-shaped pattern and thus leave the shape open ended. In this way the liquid flow can be facilitated between the front portion A and the middle B portion. Further, the embossing pattern forms two substantially U-shaped portions 181; 182 in the rear portion C. The U-shaped portions curve back towards the middle portion B of the article in proximity of the lower edge 430 of the core 4. In this way the article will conform to the anatomy of the user and the comfort of the article is improved.

Figure 2:
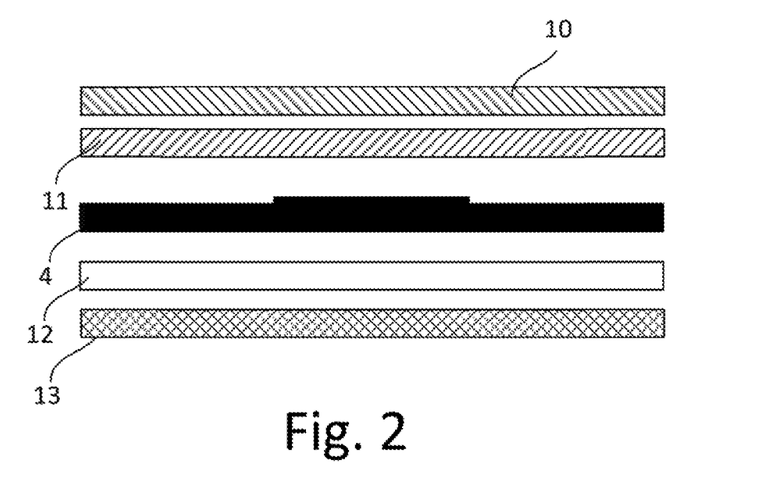
FIG. 2 shows schematically layers of an absorbent article according to the present disclosure in a cross section.

The disposable hygiene article may comprise additional embossing patterns 191; 192; 193; 194. The additional patterns may locate in at least one of the front portion A, the transitional area between the front portion A and the middle portion B, and/or the middle portion B. In the embodiment shown in FIG. 1, the embossing patterns 191; 192 are short curved lines, which follow the curvature of the longitudinally extending lines 151; 152 in the transition region 111; 112 and have a length that extends only in the front portion A and a middle portion B. Thus the embossing patterns 191; 192 are shorter than the longitudinally extending lines 151; 152. The embossing pattern 193 is a heart-shaped portion located in the front portion A in a region between an upper end edge 420 of the core 4 and the upper part of the open ended heart-shaped portion 170. A further curved line 194 extending substantially in a transversal direction T of the article is provided between the heart-shaped embossing pattern 193 and the upper end edge 420 of the core 4. The additional embossing patterns further improve the comfort of the article and assist in regulating the flow of the liquid inside the article. The flow of the liquid may be further regulated by an article which further comprises a liquid acquisition sheet 11 located next to topsheet 10 and towards the core 4, as shown in FIG. 2. Also, the article may comprise a further protective sheet 12 which is arranged between the absorbent core 4 and the liquid-impermeable backsheet 13. The protective sheet 12 is thus located beneath the absorbent core 4 directly adjacent to and in contact with the absorbent core 4, when looking at the article so that the topsheet is located uppermost and the backsheet lowermost.

Figure 3:
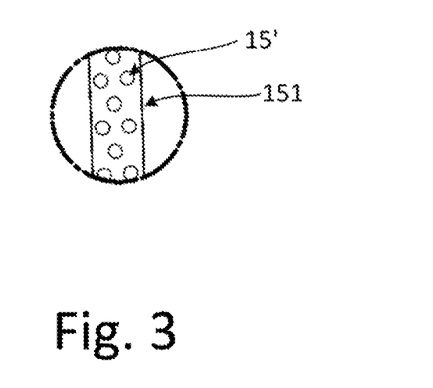
FIG. 3 shows an embossing line structure in an enlarged view.

The embossing lines are suitably obtained by means of high compression embossing. Thus, the embossing pattern will be retained also during the use of the article. As shown in FIG. 3, the embossing line 151 is suitably formed by means of an embossing pattern comprising individual circles 15' placed in a predetermined pattern having an equal diagonal and lateral mutual distance from each other. Embossing occurs before the marriage, i.e. attachment, of the backsheet layer to other layers of the absorbent article. The topsheet and the protective layer, and all layers disposed there between are embossed. However, the backsheet is not subjected to embossing. All the embossing lines may be provided in a similar way. In this way the production process and the stability of the embossing pattern during the use of the article are improved.

Returning to the core, the grammage of the absorbent material in the first area may be for example from 400-600 $g/m^2$ and the grammage of the absorbent material in the second area may be from 600-900 $g/m^2$. In this way the comfort and the absorbent properties of the article can be improved. As mentioned above, the absorbent material in the core is suitably free of super absorbent polymers (SAP). By providing the second area of the core so that it is thicker than the first area of the core and wherein the thickness of the first area of the core is from 3 to 7 mm and the thickness of the second area of the core is from 7 to 10 mm, an optimal comfort can be provided while the absorbent properties of the article are improved. Since the second area is thicker than the first area, the article can still be invisible through a garment of the user during use, which improves the comfort of the article.

The present article is adapted for three-fold, which means that the product comprises two transversally extending folding axes to enable folding of the article into three portions. In the article, the folding axes for the three-fold are preferably located longitudinally outside the transversal embossing lines 161; 162 towards the longitudinal ends 20 and 30 of the article. In the embodiment shown in FIG. 1, the folding axes correspond to the lines dividing the article into front portion A, middle portion B and rear portion C. In this way, the second area 42 of the article is kept unacted during the manufacture and transport of the article whereby optimal absorbent properties of the core are maintained during use. Also the second area of the core is preferably free of high compression embossing.

The disposable article described above may be manufactured by first feeding a liquid-permeable topsheet material, a liquid-impermeable backsheet material and an absorbent material in between the topsheet material and the backsheet material. Before the marriage, i.e. the attachment, of the backsheet material to the other layers, the absorbent core is formed so that it comprises a first area and a second area by feeding in a continuous flow absorbent material to form the core, whereby a larger amount of the absorbent material is formed in the second area of the core than is formed the first area of the core. The absorbent material is formed such that the first area is arranged to surround the second area located centrally in the middle portion B and extending longitudinally along the centre axis L, symmetrically in a transverse direction towards each side edge of the core and in a thickness direction of the article such that it protrudes outwards from the plane of the first area. The second area is formed such that it covers from 5-15% of a total area of the core and such that the first area surrounds the second area and covers the remainder of the total area of the core. The second area has a grammage higher than the first area. The increased amount and thus the higher grammage of the second area is obtained by having forming molds in the manufacturing process that are configured to hold more material in the second area than is held in the first area. Thus, the design of the molds enables the distribution of absorbent material in the present core into two different areas. The second area is integrated with the first area since the absorbent material is fed in a same material flow as the first area. The method may further comprise providing a liquid acquisition sheet next to topsheet and towards the core, and providing a protective sheet between the liquid-impermeable backsheet and the absorbent core to protect the core and embossing equipment during embossing. These additional layers are also embossed during the embossing.

After forming the different layers of the article the layers, except the backsheet layer and optional layers directly attached thereto such as release paper, are embossed with a discontinuous embossing pattern that conforms to the shape of the second area of the core as defined above. The pattern comprises two longitudinal and two transversal embossing lines that surround the second area. The embossing occurs before the marriage of the back sheet to the other layers of the article which means that any layers that are applied to the backsheet, such as release layer, are also not part of the embossing process. Thus, the backsheet layer and optional further layers attached thereto is/are not embossed before the marriage or attachment of the core layer, top sheet layer and optional layers including the acquisition sheet layer and protective sheet layer. The embossing is performed such that the second area is substantially free of compression during the embossing. Suitably, embossing is performed through the topsheet, i.e. the topsheet layer. After embossing, the backsheet layer is attached to the embossed topsheet layer, absorbent core layer and optional further layers. The attachment can be performed in a conventional way as generally described previously. The absorbent core is suitably formed into the final shape before the marriage of the sheets or layers. Also, the further optional layers that have a shape different from the outer contours of the final product can be cut before the marriage of the backsheet to the other layers. All attached layers are then cut to form a final disposable hygiene article. The cutting procedures can also be performed in any suitable conventional way.

The core forming step may comprise compression of the core. The core compression may occur in three stages. All areas, i.e. both the first and second areas of the core can be compressed during a first stage. The first area is further compressed during a second stage in which the second area is protected from too much compression. The first area is compressed even more during the high compression embossing. However, the second area is protected from further compression during the embossing stage, which is suitably high compression embossing stage.

After the article is formed, the method may further comprise folding the article by means of a three-fold also called tri-fold, in which the article is folded along two transversal folding axes that are arranged longitudinally outside the transversal embossing lines towards the longitudinal ends of the article. In this way the product is folded into three portions. The article may be packaged so that it is wrapped with a plastic film. Thus a package containing the disposable hygiene article is obtained. The disposable hygiene article in the package can be folded.

The features specified above may, within the framework of the invention defined in the appended claims, be combined between different embodiments specified.

The invention claimed is:

1. A disposable hygiene article comprising a liquid-permeable topsheet, a liquid-impermeable backsheet and an absorbent core comprising an absorbent material, the core being arranged between the topsheet and the backsheet, the article having a longitudinal center axis dividing the article into a first and a second longitudinal portion which have a symmetrical and mirror imaged shape in relation to each other, and wherein the article comprises a front portion, a middle portion and a rear portion arranged along the longitudinal center axis of the article, each of the front, the middle, and the rear portions having an individual shape, the article being adapted for three-fold along transverse folding axes that divide the article into the front, middle and rear portions, wherein the absorbent core comprises a first area and a second area, the second area being located centrally in the middle portion and extending longitudinally along the center axis, transversally and symmetrically in a transverse direction towards each side edge of the core and in a thickness direction of the article such that the second area protrudes outwards from a plane of the first area, the second area covering from 5-15% of a total area of the core, the first area surrounding the second area and covering the remainder of the total area of the core, the second area having a grammage higher than the grammage of the first area and wherein the second area is integrated with the first area, and wherein the second area is surrounded by a discontinuous embossing pattern which conforms to the shape of the second area of the core, wherein the discontinuous embossing pattern comprises two longitudinally extending embossing lines, one on each side of the second area, and two distinct transversal lines in proximity of each longitudinal end of the second area, and wherein the transversal embossing lines are shorter than a transversal distance between the longitudinally extending embossing lines, and wherein the folding axes for the three-fold are located longitudinally spaced from the transversal embossing lines.

2. The disposable hygiene article of claim 1, wherein the grammage of the absorbent material in the first area is from 400-600 g/m².

3. The disposable hygiene article of claim 1, wherein the grammage of the absorbent material in the second area is from 600-900 g/m².

4. The disposable hygiene article of claim 1, wherein the second area of the core has substantially an oval shape and has a longer extension in a longitudinal direction than in the transverse direction.

5. The disposable hygiene article of claim 1, wherein the embossing pattern corresponds to a substantially convex pattern in the middle portion and transitions to a concave pattern in a transition region between the front portion and the middle portion.

6. The disposable hygiene article of claim 1, wherein the embossing pattern corresponds to a substantially open ended heart-shaped pattern in the front portion, wherein the longitudinally extending embossing lines taper to form a concave pattern in a transition region between the front portion and the middle portion.

7. The disposable hygiene article of claim 1, wherein the embossing pattern forms two substantially U-shaped portions in the rear portion.

8. The disposable hygiene article of claim 1, wherein the hygiene article comprises additional embossing patterns in at least one of the front portion, a transition region between the front portion and the middle portion, and/or the middle portion.

9. The disposable hygiene article of claim 1, wherein the article further comprises a liquid acquisition sheet located next to the topsheet and towards the core, and wherein a further protective sheet is arranged between the liquid-impermeable backsheet and the absorbent core.

10. The disposable hygiene article of claim 1, wherein the absorbent material in the core is free of super absorbent polymers (SAP).

11. The disposable hygiene article of claim 1, wherein the second area of the core is thicker than the first area of the core and wherein a thickness of the first area of the core is from 3 to 7 mm and a thickness of the second area of the core is from 7 to 10 mm.

12. The disposable hygiene article of claim 1, wherein the embossing lines are obtained by means of high compression embossing.

13. The disposable hygiene article of claim 12, wherein the embossing lines are formed by means of an embossing pattern comprising individual circles placed in a predetermined pattern having an equal diagonal and lateral mutual distance from each other.

14. The disposable hygiene article of claim 12, wherein the second area of the core is free of high compression embossing.

15. A package containing the disposable hygiene article of claim 1, wherein the disposable article is folded.

16. The disposable hygiene article of claim 1, wherein the folding axes for the three-fold are located longitudinally outside the transversal embossing lines towards longitudinal ends of the article.

* * * * *

UNITED STATES PATENT AND TRADEMARK OFFICE
CERTIFICATE OF CORRECTION

PATENT NO. : 10,940,053 B2
APPLICATION NO. : 16/479759
DATED : March 9, 2021
INVENTOR(S) : Hood et al.

It is certified that error appears in the above-identified patent and that said Letters Patent is hereby corrected as shown below:

On the Title Page

Under abstract "16 Claims, 3 Drawing Sheets" should read --20 Claims, 3 Drawing Sheets--.

In the Specification

In Column 2, Lines 53-54, change "and the manufacture of the article is facilitated and made for flexible." to --and the manufacture of the article is facilitated and made more flexible.--.

In Column 10, Line 12, change "middle portion B an rear portion C in the'" to --middle portion B and rear portion C in the--.

In Column 11, Lines 65-67, change "whereby a larger amount of the absorbent material is formed in the second area of the core than is formed the first area of the core." to --whereby a larger amount of the absorbent material is formed in the second area of the core than is formed in the first area of the core.--.

In the Claims

Column 14, below Line 52, add Claims 17, 18, 19 and 20 as follows:
17. A method for the manufacture of the disposable article according to claim 1, comprising the steps of:
    feeding a liquid-permeable topsheet material layer, a liquid-impermeable backsheet material layer and an absorbent material layer arranged to be positioned in between the topsheet material layer and the backsheet material layer;
    forming the absorbent core so that the absorbent core comprises the first area and the second area by feeding in a continuous flow of the absorbent material to form the core, whereby a larger amount of the absorbent material is formed in the second area of the core than is formed in the first area of the core, wherein the absorbent material is formed such that the first area surrounds the second area located centrally in the middle portion and extends longitudinally along the centre axis of the Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office* article to be produced, symmetrically in the transverse direction towards each side edge of the core and in the thickness direction of the article such that the second area protrudes outwards from the plane of the first area, the second area covering from 5-15% of a total area of the core, the first area surrounding the second area and covering the remainder of the total area of the core, the second area having grammage higher than the first area and wherein the second area is integrated with the first area; and     embossing the discontinuous embossing pattern to the layers comprising the topsheet layer and the absorbent core, the discontinuous embossing pattern conforming to the shape of the second area of the core, the discontinuous embossing pattern comprising the two longitudinal embossing lines one on each side of the second area, and the two distinct transversal embossing lines in proximity of each longitudinal end of the second area such that the longitudinal embossing lines and the transversal embossing lines surround the second area, wherein the transversal embossing lines are shorter than the transversal distance between the longitudinally extending embossing lines and are located longitudinally spaced from the folding axes for the three-fold, and wherein the second area is free of compression during the embossing.

18. The method according to claim 17, wherein the method further comprises folding the article by means of the three-fold along folding axes that are arranged longitudinally outside the transversal embossing lines towards the longitudinal ends of the article.

19. The method according to claim 17, wherein the method further comprises providing a liquid acquisition sheet next to the topsheet and towards the core, and providing a protective sheet between the backsheet and the absorbent core to protect embossing equipment during embossing.

20. The method of claim 17, the transversal embossing lines being located longitudinally inward of the folding axes for the three-fold.